(12) United States Patent
Abe

(10) Patent No.: US 9,576,350 B2
(45) Date of Patent: Feb. 21, 2017

(54) MEDICAL IMAGE PROCESSING APPARATUS, X-RAY DIAGNOSTIC APPARATUS, MEDICAL IMAGE PROCESSING METHOD AND X-RAY DIAGNOSTIC METHOD

(71) Applicant: Toshiba Medical Systems Corporation, Otawara-shi (JP)

(72) Inventor: Shingo Abe, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 360 days.

(21) Appl. No.: 14/494,657

(22) Filed: Sep. 24, 2014

(65) Prior Publication Data

US 2015/0010221 A1   Jan. 8, 2015

Related U.S. Application Data

(63) Continuation of application No. PCT/JP2013/063266, filed on May 13, 2013.

(30) Foreign Application Priority Data

May 21, 2012 (JP) ................... 2012-115200

(51) Int. Cl.
*G06T 5/00* (2006.01)
*G06T 5/50* (2006.01)
(Continued)

(52) U.S. Cl.
CPC .............. *G06T 5/50* (2013.01); *A61B 6/481* (2013.01); *A61B 6/504* (2013.01); *A61B 6/5205* (2013.01);
(Continued)

(58) Field of Classification Search
CPC .......... G06T 5/50; G06T 11/008; G06T 5/004; G06T 2207/20224; G06T 2207/30101; G06T 2207/30004; G06T 2207/10116; G06T 2211/404; A61B 6/481; A61B 6/504; A61B 6/5205; A61B 6/5258; A61B 6/5264; A61B 6/542
See application file for complete search history.

(56) References Cited

U.S. PATENT DOCUMENTS 4,611,340 A * 9/1986 Okazaki ................. A61B 6/469
                                                        348/E5.089
4,633,307 A * 12/1986 Honda ................... A61B 6/504
                                                        378/98.12
(Continued)

FOREIGN PATENT DOCUMENTS

JP       03-182233 A      8/1991
JP    2010-193975 A      9/2010
(Continued)

OTHER PUBLICATIONS

Translation of the International Preliminary Report on Patentability issued Dec. 4, 2014 in PCT/JP2013/063266.
(Continued)

*Primary Examiner* — Manav Seth
(74) *Attorney, Agent, or Firm* — Oblon, McClelland, Maier & Neustadt, L.L.P.

(57) ABSTRACT

According to one embodiment, a medical image processing apparatus includes a subtraction image acquisition part, a threshold processing part, an image processing part and an image operation part. The subtraction image acquisition part is configured to acquire subtraction image data between X-ray contrast image data and X-ray non-contrast image data of an object. The threshold processing part is configured to perform threshold processing of the subtraction image data or image data generated based on the subtraction image data. The image processing part is configured to perform image processing of image data after the threshold process-
(Continued)

ing. The image operation part is configured to generate image data for a display by an image operation between the subtraction image data and image data after the image processing.

9 Claims, 6 Drawing Sheets

(51) Int. Cl.
*A61B 6/00* (2006.01)
*G06T 11/00* (2006.01)

(52) U.S. Cl.
CPC ............ *A61B 6/5258* (2013.01); *G06T 5/004* (2013.01); *G06T 11/008* (2013.01); *A61B 6/5264* (2013.01); *G06T 2207/10116* (2013.01); *G06T 2207/20224* (2013.01); *G06T 2207/30101* (2013.01); *G06T 2211/404* (2013.01)

(56) References Cited

U.S. PATENT DOCUMENTS

| | | | | |
|---|---|---|---|---|
| 5,233,989 | A * | 8/1993 | Honda | G06T 5/50 600/425 |
| 6,005,917 | A * | 12/1999 | Andersson | A61B 6/481 348/E5.088 |
| 6,195,450 | B1 * | 2/2001 | Qian | A61B 6/463 378/98.11 |
| 6,574,500 | B2 * | 6/2003 | Keren | A61B 6/504 378/51 |
| 7,158,610 | B2 * | 1/2007 | Mostafavi | A61B 6/4441 378/62 |
| 7,269,246 | B2 * | 9/2007 | Ohishi | A61B 6/504 378/196 |
| 7,496,175 | B2 * | 2/2009 | Sakaguchi | A61B 6/4233 378/95 |
| 7,604,404 | B2 * | 10/2009 | Ohishi | A61B 6/4441 378/197 |
| 7,620,146 | B2 * | 11/2009 | Mostafavi | A61B 6/4441 378/62 |
| 7,702,074 | B2 * | 4/2010 | Sakaguchi | A61B 6/481 378/4 |
| 7,792,346 | B2 * | 9/2010 | Lienard | G06T 5/50 382/128 |
| 8,265,390 | B2 * | 9/2012 | Dube | G06K 9/342 382/131 |
| 8,285,014 | B2 * | 10/2012 | Lauritsch | A61B 6/4441 378/4 |
| 8,299,413 | B2 * | 10/2012 | Vogt | G06T 5/50 250/208.1 |
| 8,355,557 | B2 * | 1/2013 | Chen | G06T 5/50 378/4 |
| 8,411,925 | B2 * | 4/2013 | Fuchigami | A61B 5/02007 378/16 |
| 8,467,587 | B2 * | 6/2013 | Burger | A61B 6/032 382/128 |
| 8,509,384 | B2 * | 8/2013 | Spahn | A61B 6/12 378/98.12 |
| 8,805,041 | B2 * | 8/2014 | Miyamoto | G06T 5/009 382/130 |
| 8,848,996 | B2 * | 9/2014 | Baumgart | A61B 5/14 128/922 |
| 9,271,688 | B2 * | 3/2016 | Das | A61B 6/481 |
| 9,330,481 | B2 * | 5/2016 | Ohishi | G06T 11/008 |
| 9,396,535 | B2 * | 7/2016 | Miyamoto | G06T 7/0014 |
| 9,433,392 | B2 * | 9/2016 | Ohishi | A61B 6/463 |
| 9,433,393 | B2 * | 9/2016 | Takemoto | A61B 6/481 |
| 2007/0036269 | A1 * | 2/2007 | Lienard | G06T 5/50 378/98.12 |
| 2007/0206724 | A1 * | 9/2007 | Sakaguchi | A61B 6/504 378/62 |
| 2008/0247503 | A1 * | 10/2008 | Lauritsch | A61B 6/4441 378/4 |
| 2009/0022271 | A1 * | 1/2009 | Ohishi | A61B 6/4441 378/19 |
| 2009/0080741 | A1 * | 3/2009 | Shinagawa | G01R 33/5601 382/131 |
| 2010/0215237 | A1 | 8/2010 | Ohishi | |
| 2011/0293164 | A1 * | 12/2011 | Sato | A61B 6/5264 382/132 |

FOREIGN PATENT DOCUMENTS

| | | |
|---|---|---|
| JP | 2011-245158 A | 12/2011 |
| JP | 2012-061307 A | 3/2012 |

OTHER PUBLICATIONS

Written Opinion issued Aug. 13, 2013 in PCT/JP2013/063266 (submitting English translation only, previously filed Sep. 24, 2014).

International Search Report mailed Aug. 13, 2013 for PCT/JP2013/063266 filed on May 13, 2013 with English Translation.

International Written Opinion mailed Aug. 13, 2013 for PCT/JP2013/063266 filed on May 13, 2013.

Combined Office Action and Search Report issued Feb. 13, 2015 in Chinese Patent Application No. 201380001249.8 (with English Translation of Category of Cited Documents).

* cited by examiner

MEDICAL IMAGE PROCESSING APPARATUS, X-RAY DIAGNOSTIC APPARATUS, MEDICAL IMAGE PROCESSING METHOD AND X-RAY DIAGNOSTIC METHOD

CROSS REFERENCES TO RELATED APPLICATIONS

This is a continuation of Application PCT/JP2013/63266, filed on May 13, 2013.

This application is based upon and claims the benefit of priority from Japanese Patent Application No. 2012-115200, filed May 21, 2012; the entire contents of which are incorporated herein by reference.

FIELD

Embodiments described herein relate generally to a medical image processing apparatus, an X-ray diagnostic apparatus, a medical image processing method and an X-ray diagnostic method.

BACKGROUND

DSA (Digital Subtraction Angiography) is known as one of imaging methods in an X-ray diagnostic apparatus. DSA is the technology to acquire subtraction image data between frames of X-ray image data before and after injecting a contrast agent into an object, for diagnosis. That is, X-ray image data is acquired before injecting a contrast agent as a mask image data for generating subtraction image data. On the other hand, X-ray contrast image data is acquired by injecting the contrast agent. Then, DSA image data is generated for diagnosis by subtraction processing between the X-ray contrast image data and the mask image data.

Such DSA image data can be generated as image data in which unnecessary shades in observation of a blood vessel are removed. That is, diagnostic image data in which blood vessels enhanced by a contrast agent are depicted selectively can be obtained. Consequently, images useful for diagnosis of a blood vessel can be displayed.

PRIOR TECHNICAL LITERATURE

[Patent literature 1] JPA 2012-61307

It is preferable that the DSA image data acquired in an X-ray diagnostic apparatus is obtained with few artifacts and a higher image quality. Note that, the DSA image data can be generated by image processing not only in a medical image processing apparatus built in an X-ray diagnostic apparatus but also in a medical image processing apparatus which is externally connected with an X-ray diagnostic apparatus.

Accordingly, an object of the present invention is to provide a medical image processing apparatus, an X-ray diagnostic apparatus, a medical image processing method and an X-ray diagnostic method which can generate DSA image data with a higher image quality.

DETAILED DESCRIPTION

In general, according to one embodiment, a medical image processing apparatus includes a subtraction image acquisition part, a threshold processing part, an image processing part and an image operation part. The subtraction image acquisition part is configured to acquire subtraction image data between X-ray contrast image data and X-ray non-contrast image data of an object. The threshold processing part is configured to perform threshold processing of the subtraction image data or image data generated based on the subtraction image data. The image processing part is configured to perform image processing of image data after the threshold processing. The image operation part is configured to generate image data for a display by an image operation between the subtraction image data and image data after the image processing.

Further, according to another embodiment, an X-ray diagnostic apparatus includes a subtraction image acquisition part, a threshold processing part, an image processing part and an image operation part. The subtraction image acquisition part is configured to acquire subtraction image data between X-ray contrast image data and X-ray non-contrast image data of an object. The threshold processing part is configured to perform threshold processing of the subtraction image data or image data generated based on the subtraction image data. The image processing part is configured to perform image processing of image data after the threshold processing. The image operation part is configured to generate image data for a display by an image operation between the subtraction image data and image data after the image processing.

Further, according to another embodiment, a medical image processing method includes acquiring subtraction image data between X-ray contrast image data and X-ray non-contrast image data of an object; performing threshold processing of the subtraction image data or image data generated based on the subtraction image data; performing image processing of image data after the threshold processing; and generating image data for a display by an image operation between the subtraction image data and image data after the image processing.

Further, according to another embodiment, an X-ray diagnostic method includes acquiring subtraction image data between X-ray contrast image data and X-ray non-contrast image data of an object; performing threshold processing of the subtraction image data or image data generated based on the subtraction image data; performing image processing of image data after the threshold processing; and generating image data for a display by an image operation between the subtraction image data and image data after the image processing.

A medical image processing apparatus, an X-ray diagnostic apparatus, a medical image processing method and an X-ray diagnostic method according to embodiments of the present invention will be described with reference to the accompanying drawings.

Figure 1:
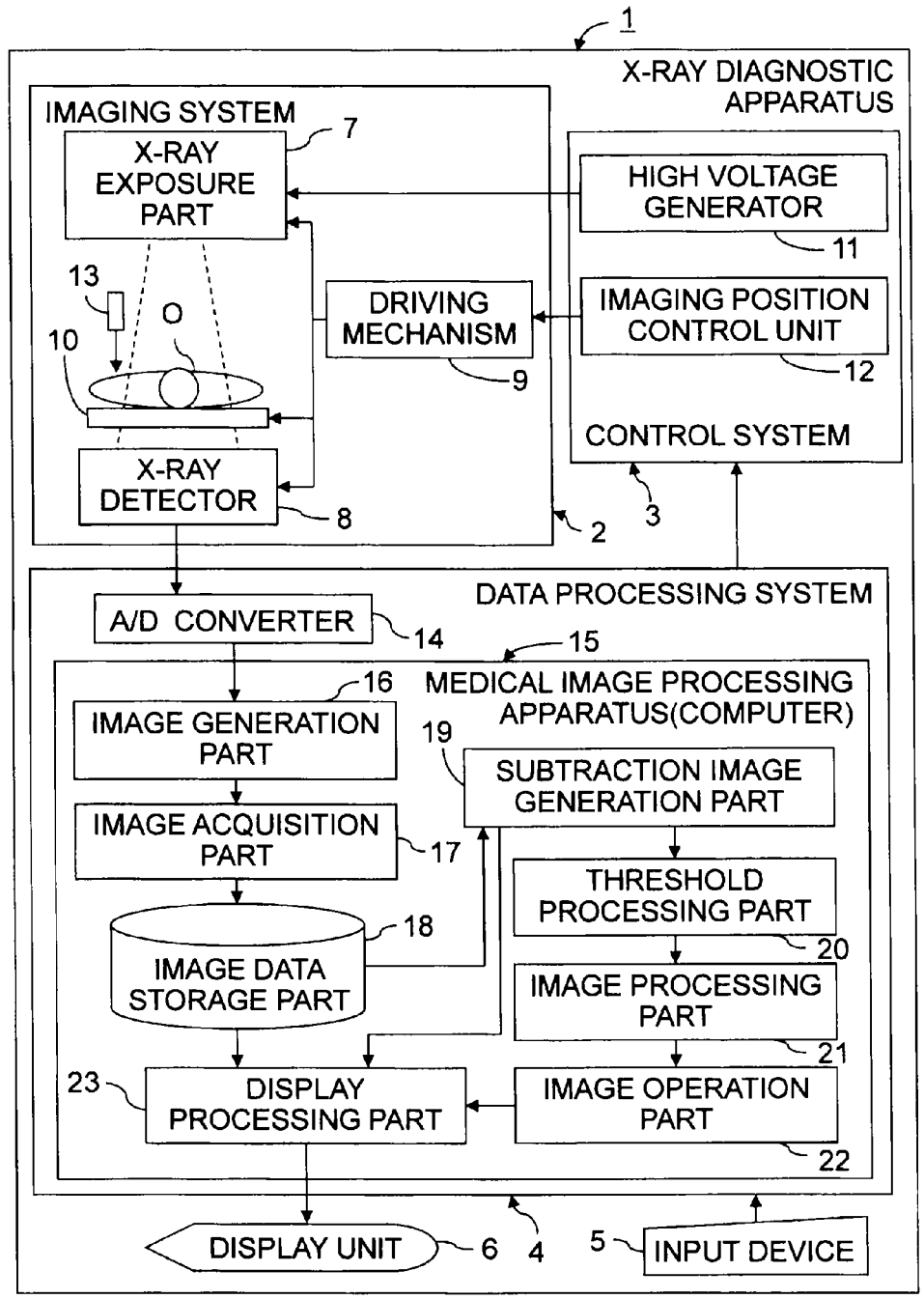
FIG. 1 is a configuration diagram of a medical image processing apparatus and an X-ray diagnostic apparatus according to one embodiment of the present invention.

FIG. 1 is a configuration diagram of a medical image processing apparatus and an X-ray diagnostic apparatus according to one embodiment of the present invention.

An X-ray diagnostic apparatus 1 includes an imaging system 2, a control system 3, and a data processing system 4, an input device 5 and a display unit 6. The imaging system 2 has an X-ray exposure part 7, an X-ray detector 8, a driving mechanism 9 and a bed 10. The control system 3 has a high voltage generator 11 and an imaging position control unit 12.

The X-ray exposure part 7 includes an X-ray tube and is placed in the opposite side of the X-ray detector 8 so that an object O set on the bed 10 lies between the X-ray exposure part 7 and the X-ray detector 8. The X-ray exposure part 7 and the X-ray detector 8 can change the angle and the relative position with respect to the object O with keeping their relative position by driving the driving mechanism 9. Specifically, the X-ray exposure part 7 and the X-ray detector 8 are settled at both ends of the C-shaped arm having the rotational function. Then, the X-ray exposure part 7 is configured to expose an X-ray from a predetermined angle to an object O by the X-ray tube to detect the X-ray having transmitted the object O by the X-ray detector 8.

Moreover, the incline and the position of the table of the bed 10 can be adjusted with the driving mechanism 9. Therefore, the radiation direction of an X-ray toward an object O can be changed by adjusting not only the angle of the X-ray exposure part 7 and the X-ray detector 8 with regard to the object O but also the angle of the table.

Furthermore, a contrast medium injector 13 is provided in the vicinity of the object O set on the bed 10 in order to inject a contrast agent into the object O.

The high voltage generator 11 of the control system 3 is a unit which applies a high voltage to the X-ray tube of the X-ray exposure part 7 to expose an X-ray, having a desired energy, toward the object O. The imaging position control unit 12 is a unit which outputs a control signal to the driving mechanism 9 to control the driving mechanism 9. That is, the inclination and position of the top plate of the bed 10, and the rotation angle and position of the X-ray exposure part 7 and the X-ray detector 8 are controlled by the control signals output to the driving mechanism 9 from the imaging position control unit 12.

The data processing system 4 has an A/D (analog to digital) converter 14 and a computer 15. The computer 15 functions as a medical image processing apparatus 15 by executing programs. That is, the medical image processing apparatus 15 is built in the X-ray imaging apparatus 1.

However, an independent medical image processing apparatus having the similar function may be connected to the X-ray imaging apparatus 1 through a network. Moreover, circuits may be used for configuring the medical image processing apparatus 15 built in the X-ray imaging apparatus 1 or the medical image processing apparatus connected with the X-ray imaging apparatus 1 through a network.

The medical image processing apparatus 15 has an image generation part 16, an image acquisition part 17, an image data storage part 18, a subtraction image generation part 19, a threshold processing part 20, an image processing part 21, an image operation part 22, and a display processing part 23.

The image generation part 16 has a function to read digitized X-ray detection data from the X-ray detector 8 through the A/D converter 14 to generate X-ray image data by data processing of the read X-ray detection data. Note that, X-ray contrast image data is to be generated when X-ray detection data is acquired with injecting a contrast agent while X-ray non-contrast image data is to be generated when X-ray detection data is acquired without injecting a contrast agent.

The image acquisition part 17 has a function to acquire the X-ray image data generated in the image generation part 16. Especially, in an independent medical image processing apparatus connected to the X-ray imaging apparatus 1 through a network, the image generation part 16 can be omitted. In this case, a function to acquire the X-ray image data from the image generation part 16 included in the X-ray imaging apparatus 1 through a network is provided with the image acquisition part 17.

The image data storage part 18 is a storage unit which stores the X-ray image data acquired by the image acquisition part 17.

The subtraction image generation part 19 has a function to generate DSA image data as subtraction image data by acquiring X-ray contrast image data and X-ray non-contrast image data of an object O, from the image data storage part 18, to perform subtraction processing. That is, X-ray contrast image data and X-ray non-contrast image data are imaged on a same position of an object O and the X-ray non-contrast image data is used as mask image data to generate the DSA image data.

Therefore, the X-ray diagnostic apparatus 1 has a function as a subtraction image acquisition part, which acquires subtraction image data between X-ray contrast image data and X-ray non-contrast image data of an object O, by the data processing system 4, including at least the image generation part 16, the image acquisition part 17 and the subtraction image generation part 19, which collaborates with the imaging system 2 and the control system 3. Moreover, the medical image processing apparatus 15 also has a function as a subtraction image acquisition part, which acquires subtraction image data between X-ray contrast image data and X-ray non-contrast image data of an object O, by elements including at least the image acquisition part 17 and the subtraction image generation part 19.

The X-ray contrast image data and the mask image data used for generating DSA image data are imaged at different timings. Therefore, when a motion occurs in the object O between the imaging timings of the X-ray contrast image data and the mask image data, a position gap arises. Therefore, when a DSA image data is generated, unnecessary signal components may remain by the position gap between image data. Then, the remaining unnecessary signal components bring artifacts on DSA images.

Accordingly, the threshold processing part 20, the image processing part 21 and the image operation part 22 in the medical image processing apparatus 15 are configured to perform data processing which reduces artifacts of DSA image data possibly generated due to a position gap caused by a movement of an object O or the like. Then, image data after the data processing in the threshold processing part 20, the image processing part 21 and the image operation part 22 is given to the display processing part 23 as diagnostic image data.

Figure 2:
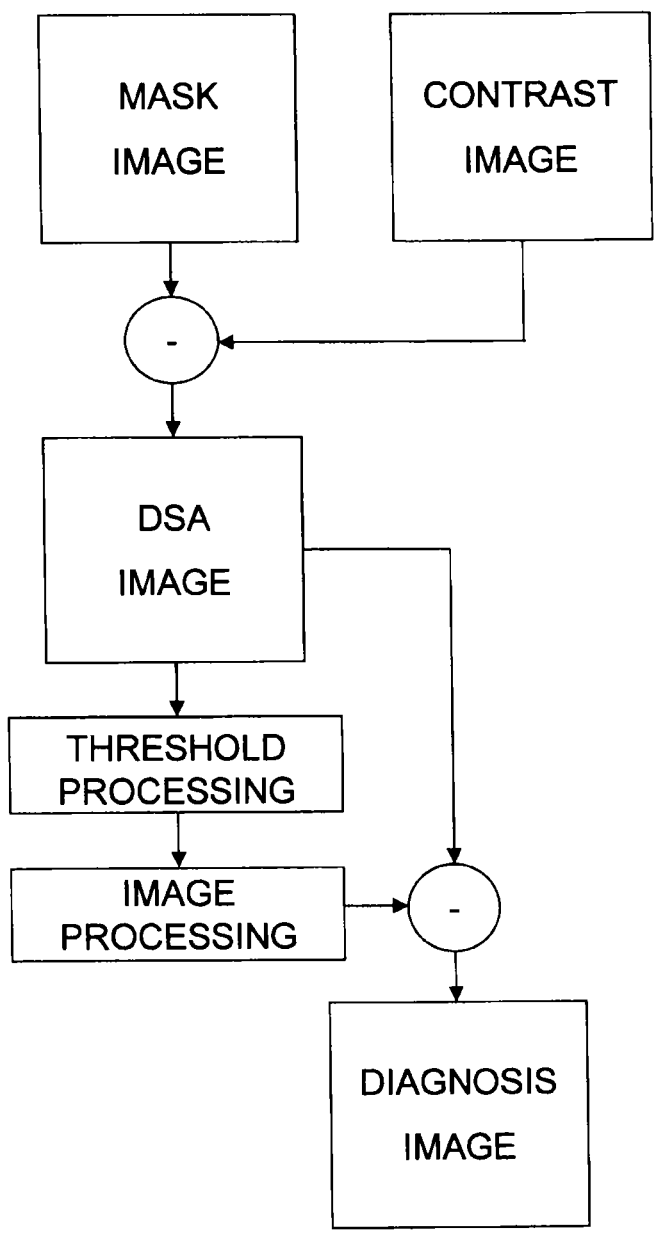
FIG. 2 is a chart for explaining a method of generating DSA image data and diagnostic image data based on the DSA image data.
Figure 3:
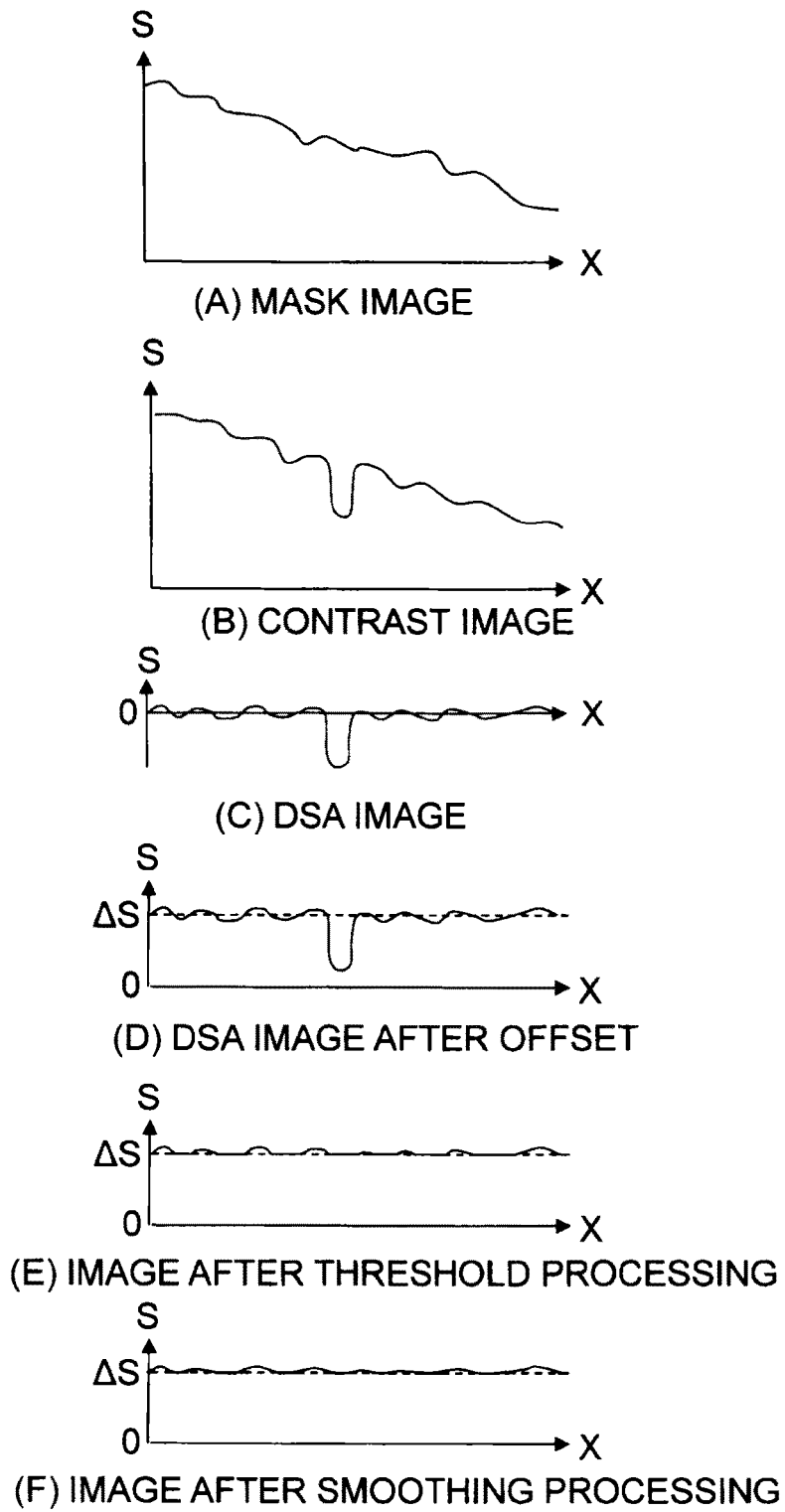
FIG. 3 shows an example of profiles of pixel values of image data in a generation process of DSA image data and diagnostic image data.
Figure 4:
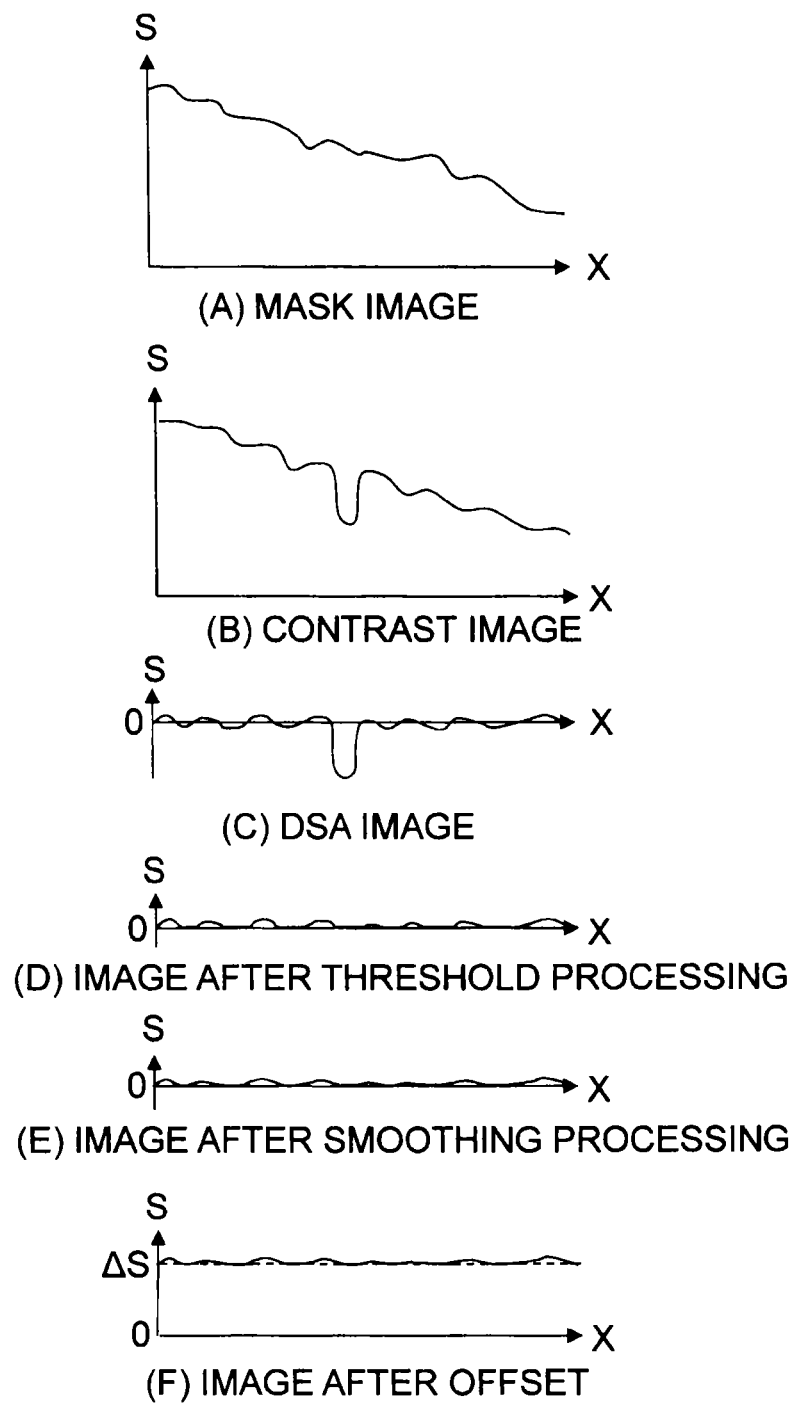
FIG. 4 shows another example of profiles of pixel values of image data in a generation process of DSA image data and diagnostic image data.

FIG. 2 is a chart for explaining a method of generating DSA image data and diagnostic image data based on the DSA image data. Moreover, FIG. 3 shows an example of profiles of pixel values of image data in a generation process of DSA image data and diagnostic image data while FIG. 4 shows another example of profiles of pixel values of image data in a generation process of DSA image data and diagnostic image data. Note that, in each graph of FIG. 3 and FIG. 4, the horizontal axis denotes one dimensional position X and the vertical axis denotes a pixel value S of image data at each position.

The mask image data acquired for generating DSA image data without injecting a contrast agent have pixel values according to respective positions as shown in FIG. 3(A) or FIG. 4(A). On the other hand, when a contrast agent is injected into a blood vessel of an object O, signal values in the blood vessel decrease. Therefore, X-ray contrast image data have lower pixel values than those of the mask image data in positions corresponding to the blood vessel and pixel values similar to those of the mask image data in positions corresponding to the background tissues, as shown in FIG. 3(B) or FIG. 4(B).

Then, as shown in FIG. 2, DSA image data can be generated by subtracting the mask image data from the X-ray contrast image data. The subtraction processing is performed in the subtraction image generation part 19 as mentioned above. As a result of the subtraction processing, the DSA image data having negative pixel values locally in the blood vessel region and pixel values close to zero in the background regions are obtained as shown in FIG. 3(C) or FIG. 4(C).

It can be considered that positive or negative pixel values in the background regions are not zero due to a position gap between the X-ray contrast image data and the mask image data caused by a motion of the object O or the like, X-ray quantum noise components by a fluctuation of X-ray photons, noise components in circuits of the X-ray detector 8 and the like. That is, if there is no noise components by factors including the position gap between the X-ray contrast image data and the mask image data, the pixel values in the background regions are ideally zero. However, the DSA image data having positive or negative pixel values in the background regions are generated by the position gap between the images and the like.

Moreover, in the subtraction image generation part 19, offset processing which adds a constant pixel value to each pixel value of the subtraction image data as shown in FIG. 3(C) can be performed as post processing of the subtraction processing so that each pixel value of the DSA image data presents a positive value. In this case, subtraction image data which shifts by a constant offset value $\Delta S$ in the positive side are obtained as DSA image data as shown in FIG. 3(D). Then, it becomes possible to display the image data, whose pixel values are positive values, on the display unit 6 by changing the pixel values into brightness values.

However, it can be considered that image signals each having a pixel value, which is not the offset value $\Delta S$, in the background regions correspond to noises or artifacts. Especially, each image signal showing a larger pixel value than the offset value $\Delta S$, among the image signals corresponding to noises or artifacts is displayed more brightly than the surrounding background tissues, in a display with brightness. Therefore, each image signal showing a larger pixel value than the offset value $\Delta S$ is glaring.

Meanwhile, the blood vessel region has pixel values smaller than the offset value $\Delta S$. Therefore, ideal DSA image data has no pixels having pixel values larger than the offset value $\Delta S$. For that reason, each pixel having a larger pixel value than the offset value $\Delta S$ can be considered as a pixel corresponding to a noise or an artifact regardless of the background tissue region or the blood vessel region.

On the other hand, in the DSA image data before the offset processing as shown in FIG. 4(C), each pixel having a positive pixel value can be considered as a pixel corresponding to a noise or an artifact regardless of the background tissue region or the blood vessel region.

The threshold processing part 20 has a function to perform threshold processing of DSA image data, generated as subtraction image data between X-ray contrast image data and X-ray non-contrast image data, or DSA image data obtained from the subtraction image data by post-processing, such as offset processing.

When the threshold processing is performed to the subtraction image data between X-ray contrast image data and X-ray non-contrast image data, it is preferable that a threshold value of the threshold processing is determined to be zero. On the other hand, when the threshold processing is performed to DSA image data after offset processing which adds a constant value to each pixel value of the subtraction image data between X-ray contrast image data and X-ray non-contrast image data, it is preferable that an offset value is determined to be a threshold value.

Then, the threshold processing is performed in the threshold processing part 20 as processing to replace each pixel value smaller than a threshold value by the threshold value. Specifically, when DSA image data after offset processing are subjected to the threshold processing, every pixel value smaller than the offset value $\Delta S$ is replaced into the offset value $\Delta S$ as shown in FIG. 3(E). On the other hand, subtraction image data are subjected to the threshold processing, every negative pixel value is replaced into zero as shown in FIG. 4(D).

That is, every pixel value corresponding to a noise or an artifact remains while the pixel values in the other regions become the offset value $\Delta S$ equivalent to the pixel value of the background tissue as shown in FIG. 3(E). Alternatively, every pixel value corresponding to a noise or an artifact remains while the pixel values in the other regions become zero equivalent to the pixel value of the background tissue as shown in FIG. 4(D). In other words, the regions corresponding to noises or artifacts can be extracted as distinct regions.

Note that, an arbitrary margin may be set to the threshold value instead of strictly setting the threshold value into the offset value $\Delta S$ or zero. That is, the threshold value may be also set to an arbitrary value close to the offset value $\Delta S$ or zero. However, setting the threshold value to not less than the pixel value corresponding to the background tissue at least can prevent an image signal corresponding to the blood vessel from being incorrectly recognized as a signal corresponding to a noise or an artifact. That is, it can be prevented that a part of blood vessel region is extracted as the distinct region.

The image processing part 21 has a function to perform image processing of image data after the threshold processing in the threshold processing part 20. More specifically, the image data after the threshold processing can be subjected to at least one of smoothing processing, processing to attenuate pixel values using a nonlinear function, threshold processing, constant multiplication processing and processing to compress a dynamic range. Examples of the compression processing of a dynamic range include constant multiplication processing to compress a dynamic range linearly and logarithmic transformation processing to compress a dynamic range nonlinearly using a logarithmic function.

Figure 5:
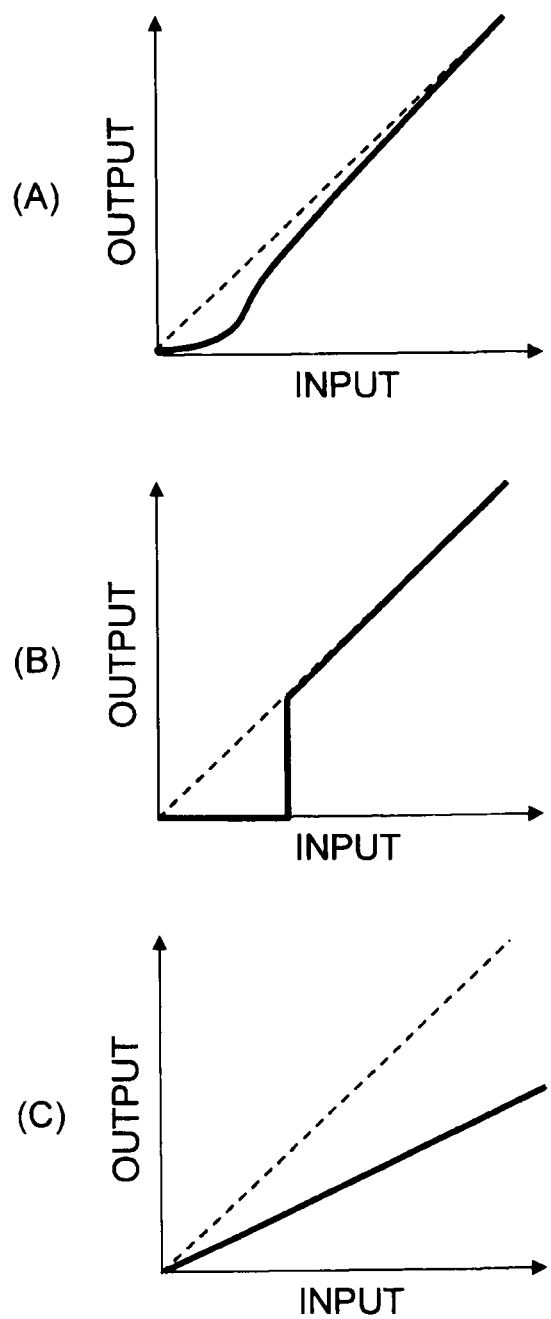
FIG. 5 shows examples of a function used for the image processing shown in FIG. 2.

FIG. 5 shows examples of a function used for the image processing shown in FIG. 2.

In FIG. 5, each horizontal axis denotes an input to a function used for image processing and each vertical axis denotes an output from the function. FIG. 5(A) shows an example of nonlinear function to attenuate pixel values. The nonlinear function can be an arbitrary function which can convert a larger part of pixel values into larger pixel values non-linearly. Specifically, an arbitrary nonlinear function, such as a high order function, a spline function, an exponential function, and a logarithmic function can be used.

FIG. 5(B) shows an example of function used for the threshold processing. As shown in FIG. 5(B), each pixel value smaller than a threshold value can be replaced into zero by the threshold processing. Moreover, FIG. 5(C) shows an example of linear function used for the constant multiplication processing. When the constant multiplication processing shown in FIG. 5(C) is performed, undulation of image data can be decreased.

The parameters for defining a function used for the image processing may be also made variable. Then, an appropriate function can be used for the image processing by adjusting the parameters. The selection of a function used for the image processing and the adjustment of the parameters can be previously performed by a simulation.

Note that, as a result of a simulation, it can be confirmed that it is preferable to perform smoothing processing as the image processing. When the smoothing processing is performed, image data after the image processing as shown in FIG. 3(F) or FIG. 4(E) are generated.

Moreover, when the offset processing has not been performed to the subtraction image data between X-ray contrast image data and X-ray non-contrast image data as post-processing, the image processing part 21 is configured to perform offset processing to add a constant value to each pixel value of the image data before or after the image processing.

That is, the frames of image data respectively generated in the subtraction image generation part 19, the threshold processing part 20 and the image processing part 21 do not be directly displayed. Therefore, the offset processing which makes all pixel values of image data positive values can be also performed before or after the image processing in the image processing part 21. When the image data after the image processing has been subjected to the offset processing by the image processing part 21, the image data as shown in FIG. 4(E) is shifted by the offset value ΔS in the positive side. Consequently, the image data as shown in FIG. 4(F) is generated.

The image operation part 22 has a function to generate diagnostic image data for a display by an image operation between the image data after the image processing in the image processing part 21 and the subtraction image data. Specifically, an image operation to subtract the DSA image data, after the threshold processing and the image processing, from the original DSA image data is performed as shown in FIG. 2. Thereby, the pixel values in the distinct regions extracted by the threshold processing are fed back to the DSA image data.

That is, the image data for a diagnosis in which noises and artifacts are reduced are generated by subtracting the data, in which undulation of the signal values corresponding to the noises and the artifacts is spatially compressed, from the DSA image data. Moreover, it can be avoided that unnatural diagnostic image data are generated since the signal values corresponding to the noises and the artifacts are not directly subtracted from the DSA image data.

Note that, data after the offset processing are subjected to the image operation. Therefore, the image data for diagnosis have positive pixel values so that the image data for diagnosis can be displayed with brightness.

The display processing part 23 has a function to perform image processing for display of diagnostic image data generated by the threshold processing part 20, the image processing part 21 and the image operation part 22 or the DSA image data generated in the subtraction image generation part 19 to display the image data on the display unit 6. Examples of the image processing for display include display processing such as gradation processing and spatial filter processing.

Next, an operation and an action of the medical image processing apparatus 15 and the X-ray diagnostic apparatus 1 will be explained.

Figure 6:
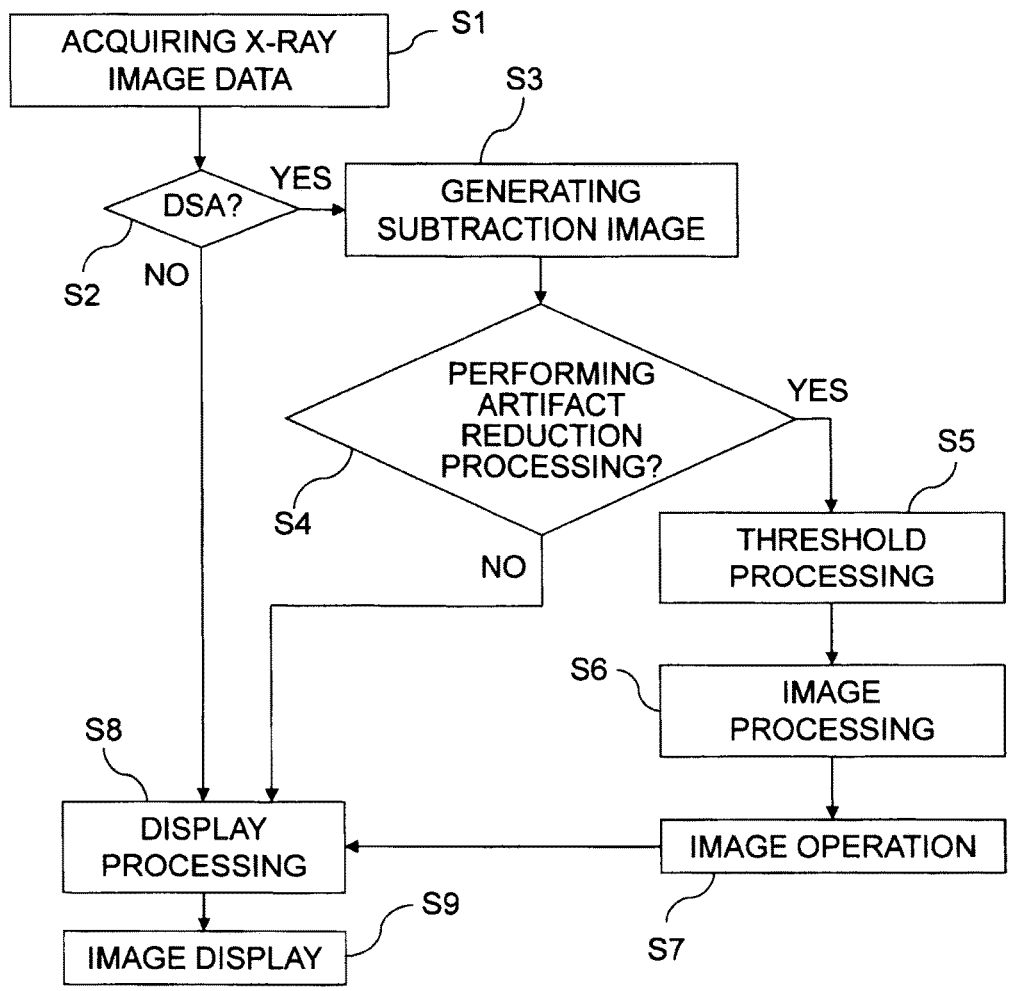
FIG. 6 is a flow chart showing a flow for acquiring and displaying DSA image data of an object by the X-ray diagnostic apparatus, in which the medical image processing apparatus is built, shown in FIG. 1.

FIG. 6 is a flow chart showing a flow for acquiring and displaying DSA image data of an object O by the X-ray diagnostic apparatus 1, in which the medical image processing apparatus 15 is built, shown in FIG. 1.

First, an acquisition and generation of DSA images is previously input into the data processing system 6 as imaging conditions and image processing conditions by operating the input device 5. Then, the imaging conditions are output to the control system 3 from the data processing system 6. Moreover, the image processing conditions are given to the medical image processing apparatus 15.

Next, in Step S1, an object O is set on the top plate of the bed 10 and X-ray image data are acquired from the object O. When DSA image data are generated, a contrast agent is injected into the object O from the contrast medium injector 13. Then, X-ray image data are acquired before and after injecting the contrast agent.

Specifically, control signals according to the imaging conditions are output from the imaging position control unit 12 of the control system 3 to drive the driving mechanism 9. Thereby, the X-ray exposure part 7 and the X-ray detector 8 are positioned to a predetermined position. On the other hand, a high voltage is applied to the X-ray tube of the X-ray exposure part 7 from the high voltage generator 11 of the control system 3. Thereby, an X-ray is exposed to an imaging part of the object O from the X-ray tube. Then, the X-ray which transmitted the object O is detected by the X-ray detector 8.

Next, an X-ray detection signal is output to the medical image processing apparatus 15 from the X-ray detector 8 through the A/D converter 14. Thereby, the digitized X-ray detection data is acquired in the image generation part 16. Then, the image generation part 16 generates X-ray image data by known data processing of the X-ray detection data.

The X-ray image data generated in the image generation part 16 is given to the image acquisition part 17. Then, the image acquisition part 17 writes and stores the acquired X-ray image data in the image data storage part 18. Note that, X-ray image data is acquired before and after injecting a contrast agent. Therefore, X-ray contrast image data and X-ray non-contrast image data are stored in the image data storage part 18.

Next, in Step S2, the medical image processing apparatus 15 determines whether the X-ray image data is for a DSA. Then, when the X-ray image data have been determined to be for the DSA with reference to the image processing conditions, in Step S3, the subtraction image generation part 19 reads the X-ray contrast image data and the X-ray non-contrast image data from the image data storage part 18 to perform subtraction processing. Thereby, subtraction image data are generated.

Next, in Step S4, the medical image processing apparatus 15 determines whether performing reduction processing of artifacts has been instructed as an image processing condition for generating DSA image data. When the reduction processing of artifacts is performed, the subtraction image data generated in the subtraction image generation part 19 are given to the threshold processing part 20.

Next, in Step S5, the threshold processing part 20 performs threshold processing of the subtraction image data. Specifically, an image signal value corresponding to a background tissue is set to a threshold value. Then, processing which replaces each pixel value, less than the threshold value, into the threshold value is performed to the subtraction image data. Consequently, noise regions and artifact regions having image signal values larger than the image signal value corresponding to the background tissue are extracted.

Next, in Step S6, the image processing part 21 performs image processing, such as smoothing processing, to reduce an undulation in signal values, of the image data after the threshold processing in the threshold processing part 20.

Next, in Step S7, the image operation part 22 generates diagnostic image data for display by an image operation between the image data after the image processing in the image processing part 21 and the subtraction image data generated in the subtraction image generation part 19. Specifically, components of noises and artifacts are removed from the subtraction image data by subtracting the image data, after the image processing, corresponding to the noises and the artifacts, from the subtraction image data. Consequently, the diagnostic image data in which artifacts are reduced can be obtained.

Next, in Step S8, the display processing part 23 acquires the diagnostic image data from the image operation part 22 to perform display processing. Note that, when it has not been determined to perform the reduction processing of artifacts in Step S4, the subtraction image data generated in the subtraction image generation part 19 is given to the display processing part 23 as the diagnostic image data. Therefore, the display processing part 23 performs display processing of the subtraction image data. Moreover, when it has not been determined that imaging is for a DSA in Step S2, the display processing part 23 reads the X-ray image data to be displayed from the image data storage part 18. Then, display processing is performed to the read X-ray image data.

Next, in step S9, the display processing part 23 outputs the diagnostic image data after the display processing to the display unit 6. Thereby, diagnostic images are displayed on the display unit 6. Thus, a user can observe the diagnostic images displayed on the display unit 6.

That is, each the medical image processing apparatus 15 and the X-ray diagnostic apparatuses 1 as described above is configured to extract noise components and artifact components by threshold processing of DSA image data, perform image processing to reduce an undulation of the extracted noise components and artifact components, and subtract the noise components and the artifact components after the image processing from the DSA image data, in order to generate diagnostic image data for display.

Consequently, according to the medical image processing apparatus 15 and the X-ray diagnostic apparatus 1, artifacts in DSA images can be reduced even when a motion or the like arises in an object O. Therefore, it becomes possible to display DSA images appropriate for a diagnosis.

Especially, it can be avoided that pixel values in a blood vessel region are extracted as noise components and artifact components, by setting a threshold value, for extracting the noise components and the artifact components, to a value not less than a pixel value corresponding to a background tissue. Consequently, adverse effects by reduction processing of artifacts that a blood vessel disappears from original DSA image data and that a blur and a density change occur can be prevented. Then, most of artifacts conspicuous as high signal regions brighter than a background part can be reduced especially.

Note that, it can be easily determined by brightness that each artifact displayed more darkly than a background part is one due to a motion of an object O. Therefore, artifacts which appear as low signal regions are not serious interference in diagnosis.

Moreover, noise components and artifact components are subtracted from subtraction image data in a state that an undulation of the noise components and the artifact components has been reduced by image processing such as smoothing processing. That is, high frequency components such as edge parts of artifacts and amplitude parts of noises are subtracted from subtraction image data in a state that the high frequency components became small relatively. Consequently, unnaturalness can be reduced compared with the case that noise components and artifact components are subtracted from subtraction image data without the image processing.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the sign of signal values of diagnostic image data finally displayed on the display unit 6 may be inverted. Processing which inverts the sign of signal values can be performed to data to be a processing target in at least one of the subtraction image generation part 19, the threshold processing part 20, the image processing part 21 and the image operation part 22.

The processing which inverts the sign of signal values may be one to invert data with centering on a constant straight line whose signal value is not zero and subsequently move the data in parallel toward the opposite quadrant side so that the sign is inverted. In that case, another data processing may be also performed between the data inversion processing and the parallel translation processing. That is, processing which inverts the sign of signal values have only to be substantially performed in at least one of the subtraction image generation part 19, the threshold processing part 20, the image processing part 21 and the image operation part 22. When the processing which inverts the sign of signal values is performed substantially, image data in which a contrast agent is depicted white as high signal values are to be generated for display in the image operation part 22.

What is claimed is:

1. A medical image processing apparatus comprising:
a subtraction image acquisition part configured to acquire subtraction image data between X-ray contrast image data and X-ray non-contrast image data of an object;
a threshold processing part configured to perform threshold processing of the subtraction image data or image data generated based on the subtraction image data;

an image processing part configured to perform image processing of image data after the threshold processing; and an image operation part configured to generate image data for a display by an image operation between the subtraction image data and image data after the image processing.

2. A medical image processing apparatus of claim 1, wherein said image processing part is configured to perform at least one processing of smoothing processing, processing to attenuate a pixel value using a nonlinear function, threshold processing, constant multiplication processing, and processing to compress a dynamic range, to the image data after the threshold processing.

3. A medical image processing apparatus of claim 1, wherein said threshold processing part is configured to perform the threshold processing using a threshold value set to not less than a pixel value corresponding to a background tissue.

4. A medical image processing apparatus of claim 1, wherein said threshold processing part is configured to perform the threshold processing of image data after offset processing which adds a constant value to each pixel value of the subtraction image data.

5. A medical image processing apparatus of claim 1, wherein said threshold processing part is configured to perform the threshold processing of the subtraction image data; and said image processing part is configured to perform offset processing which adds a constant value to each pixel value of image data before or after the image processing.

6. A medical image processing apparatus of claim 1, wherein at least one of said subtraction image acquisition part, said threshold processing part, said image processing part, and said image operation part is configured to perform processing which substantially inverts a sign of each signal value of data to be a processing target; and said image operation part is configured to generate the image data for the display as image data in which a contrast agent is depicted as a high signal value.

7. An X-ray diagnostic apparatus comprising:

a subtraction image acquisition part configured to acquire subtraction image data between X-ray contrast image data and X-ray non-contrast image data of an object;

a threshold processing part configured to perform threshold processing of the subtraction image data or image data generated based on the subtraction image data;

an image processing part configured to perform image processing of image data after the threshold processing; and an image operation part configured to generate image data for a display by an image operation between the subtraction image data and image data after the image processing.

8. A medical image processing method comprising:

acquiring subtraction image data between X-ray contrast image data and X-ray non-contrast image data of an object;

performing threshold processing of the subtraction image data or image data generated based on the subtraction image data;

performing image processing of image data after the threshold processing; and generating image data for a display by an image operation between the subtraction image data and image data after the image processing.

9. An X-ray diagnostic method comprising:

acquiring subtraction image data between X-ray contrast image data and X-ray non-contrast image data of an object;

performing threshold processing of the subtraction image data or image data generated based on the subtraction image data;

performing image processing of image data after the threshold processing; and generating image data for a display by an image operation between the subtraction image data and image data after the image processing.

* * * * *